(12) United States Patent
Bucur et al.

(10) Patent No.: US 10,657,613 B2
(45) Date of Patent: May 19, 2020

(54) IDENTITY MATCHING OF PATIENT RECORDS

(75) Inventors: Anca I. D. Bucur, Eindhoven (NL); Richard Vdovjak, Eindhoven (NL); Jasper J. A. Van Leeuwen, Eindhoven (NL)

(73) Assignee: Koninklijke Philips N.V. (NL)

(*) Notice: Subject to any disclaimer, the term of this patent is extended or adjusted under 35 U.S.C. 154(b) by 1105 days.

(21) Appl. No.: 13/700,743

(22) PCT Filed: Jun. 10, 2011

(86) PCT No.: PCT/IB2011/052548
§ 371 (c)(1),
(2), (4) Date: Nov. 29, 2012

(87) PCT Pub. No.: WO2011/158163
PCT Pub. Date: Dec. 22, 2011

(65) Prior Publication Data
US 2013/0080192 A1    Mar. 28, 2013

(30) Foreign Application Priority Data
Jun. 17, 2010 (EP) .................................... 10166325

(51) Int. Cl.
*G06Q 50/24* (2012.01)
*G16H 10/60* (2018.01)
*G16H 50/20* (2018.01)

(52) U.S. Cl.
CPC ............ *G06Q 50/24* (2013.01); *G16H 10/60* (2018.01); *G16H 50/20* (2018.01)

(58) Field of Classification Search
CPC .............. G06Q 50/22–24; G06Q 50/24; G06F 17/30864; G06F 19/345; G06F 19/322; G16H 10/60
See application file for complete search history.

(56) References Cited

U.S. PATENT DOCUMENTS

| 8,495,069 B2* | 7/2013 | Friedlander et al. .......... 707/748 |
| 2003/0046280 A1* | 3/2003 | Rotter .................... G06F 19/322 |

(Continued)

FOREIGN PATENT DOCUMENTS

| WO | 0122285 A2 | 3/2001 |
| WO | 03046798 A1 | 6/2003 |
| WO | 2006015340 A2 | 2/2006 |

OTHER PUBLICATIONS

Forrey et al, "Logical Observation Identifier Names and Codes (LOINC) Database: A Public Use Set of Codes and Names for Electronic Reporting of Clinical Laboratory Test Results", Clinical Chemistry, vol. 42, No. 1, 1996, pp. 81-90.

(Continued)

*Primary Examiner* — Sheetal R Paulson

(57) ABSTRACT

A system for matching a pair of patient records as belonging to the same individual or patient is disclosed. A set of matching rules (4) represents persistent characteristics of clinical properties of patients. A clinical property extractor (5) is used for extracting at least one first clinical property from clinical information contained in the first patient record (1) and at least one second clinical property from clinical information contained in the second patient record (2). A match detector (3) is used for detecting whether the first patient record (1) and the second patient record (2) relate to the same patient, based on the first clinical property, the second clinical property, and the set of matching rules 4. A demographic property extractor (6) is used for extracting demographic data.

20 Claims, 2 Drawing Sheets

(56) References Cited

U.S. PATENT DOCUMENTS

| | | |
|---|---|---|
| 2003/0088438 A1* | 5/2003 | Maughan et al. ................ 705/2 |
| 2005/0004895 A1* | 1/2005 | Schurenberg et al. ........... 707/3 |
| 2005/0158767 A1 | 7/2005 | Haskell et al. |
| 2007/0299697 A1 | 12/2007 | Friedlander et al. |
| 2011/0004626 A1* | 1/2011 | Naeymi-Rad et al. ....... 707/776 |

OTHER PUBLICATIONS

Malin et al, "How (Not) to Protect Genomic Data Privacy in a Distributed Network: Using Trail Re-Identification to Evaluate and Design Anonymity Protection Systems", Journal of Biomedical Informatics, 37, 2004, pp. 179-192.

Teich, "Clinical Information Systems for Integrated Healthcare Networks", Clinical Systems Research & Development, Partners Healthcare Systems, 1998, pp. 19-28.

Grannis et al, "Analysis of a Probabilistic Record Linkage Technique Without Human Review", AMIA Symposium Proceedings, 2003, pp. 259-263.

Winkler, W.E. "The State of Record Linkage and Current Research Problems", U. S. Bureau of the Census, 1999.

Winkler, W.E. "Record Linkage Software and Methods for Merging Administrative Lists", U.S. Bureau of the Census, 2001.

Bell, G.B. et al. "In a National Medical Patient Index Matching Records", Communications of the ACM Sep. 2001/vol. 44, No. 9.

\* cited by examiner

IDENTITY MATCHING OF PATIENT RECORDS

FIELD OF THE INVENTION

The invention relates to identity matching of patient records.

BACKGROUND OF THE INVENTION

Patients receiving care at several healthcare organizations may receive several distinct patient identifiers, usually one at each autonomous healthcare organization that they visit. The patient data, such as electronic medical records, medical images, and other relevant medical information are spread across multiple sites. In order to be able to retrieve all relevant patient data regardless of the healthcare site where these data were captured and stored, the patient identifiers at the various sites and the respective patient records should be linked, without requiring the sites to adopt a common patient identifier.

The volume of data collected for a patient in the context of a complex disease such as cancer has increased tremendously, and a large portion of these data, describing the medical history of a patient, can be relevant for diagnosis and treatment of the patient. In the case of recurring cancer patients, the relevant cancer-related health episodes can go many years back. Comorbidities are often relevant as well, as they may be a constraining factor for choosing a therapy. For example, many chemotherapy agents are cardiotoxic, and in order to choose the right therapy, prior information concerning cardiac disease may be important. It is highly unlikely that the information about all these health-related episodes of a patient resides in the system of a single institution. However, the treating clinician seeing a patient should be able to extract all the relevant prior health episodes from the patient record, cancer-related as well as and non-cancer-related episodes. Each patient record may include many episodes and span a few decades.

The flow of information into and out of the patient record is typically channeled through a Master Patient Index (MPI) that associates a unique medical record number (MRN) with each patient entity when a unit record exists. To obtain a view on patients across distributed data sources, the local identifiers in the individual institutions need to be reconciled. This is currently done by building an MPI that interrelates all the identifiers in hospitals that are part of a collaborating group, or enterprise. An Enterprise Master Patient Index (EMPI) is developed through integration of the individual MPIs of the sources. Generally, the integration is achieved by comparing demographic attributes such as first/last name, gender, date of birth, address etc., to create an enterprise-level identifier, and is rarely based on a single identifier shared across the different organizations in the enterprise. Most of the existing systems deploy probabilistic algorithms which typically compare a fixed record with a number of candidates for a match, computing for each candidate a likelihood ratio (weighted score) that is compared to chosen accept and reject thresholds. This is used to decide whether to link the records or not. When the decision cannot be taken automatically (the computed likelihood falls between the accept and reject thresholds), qualified personnel reviews or flags the potential (mis)matches before they are accepted (or rejected). However, submitting a large amount of records for manual review is very costly and may make the solution impractical.

The number of matches automatically rejected, accepted, or submitted for manual review depends both on the weights associated with the different attributes during comparison, on the basis of which the likelihood ratio is computed, and on the chosen reject and accept thresholds. The matching process is tuned with these thresholds by trading off data consistency versus completeness. The pairs of records having scores between the reject and accept threshold are submitted for manual review, which means that a clinical expert or dedicated personnel needs to manually review those records and decide on whether to match them, or even ask the patient whether the two records belong to him or her. With a conservative approach, when both false positives and false negatives need to be avoided, this may constitute a high cost for the healthcare organization. Also, when matching across large medical record systems and other data sources such as PACS and lab systems, and when large amounts of data need to be manually reviewed and matched for each pair of potentially matching records, the number of erroneous matches may go up.

S. J. Grannis et al., "Analysis of a probabilistic Record Linkage Technique without Human Review", AMIA 2003 Symposium Proceedings, pages 259-263, discloses record linkage using probabilistic linkage techniques. Grannis et al. further discloses avoiding human review in such methods by means of an estimator function using an expectation maximization algorithm to establish a single true-link threshold.

SUMMARY OF THE INVENTION

It would be advantageous to have an improved system for matching a pair of patient records as belonging to the same individual or patient. To better address this concern, in a first aspect, the invention provides a system comprising:

a set of matching rules representing persistency characteristics of clinical properties of patients;

a clinical property extractor for extracting at least one first clinical property from clinical information contained in the first patient record and at least one second clinical property from clinical information contained in the second patient record;

a match detector for detecting whether the first patient record and the second patient record relate to the same patient, based on the first clinical property, the second clinical property, and the set of matching rules.

The accuracy and the stability of the demographic data have their limitations and may include errors. For example, people change address, family names may change after marriage, individuals may have several nick names, registration personnel may introduce errors in the data entered in the patient record, patients may refuse to provide their social security number or provide an incorrect one. On the other hand, clinical data follows predetermined persistency rules. For example, the blood group of a patient normally does not change. Consequently, a comparison of the blood group mentioned in two patient records can be used either to reinforce the certainty of a match (if the blood group is the same) or to reject a match (if the blood group is different). Also, some clinical events leave permanent traces, such as antibodies, in the body, which should be present in future clinical tests. This allows establishing the set of matching rules based on persistency characteristics of clinical properties of patients. Using these matching rules and clinical information may improve the record matching and/or reduce the number of records submitted for manual evaluation.

The system may comprise a demographic property extractor for extracting first demographic data from the first patient record and second demographic data from the second patient record, wherein the match detector is arranged for performing the detecting also based on the first demographic data and the second demographic data. This way, the clinical data and the demographic data are both used, which further improves the record matching.

The set of matching rules may be associated with a set of corresponding weights. Moreover, the match detector may be arranged for determining a matching score for the pair of patient records, based on the set of matching rules and the set of corresponding weights. This way, different matching rules may be combined. Moreover, it allows computing a matching score indicating a confidence level of the match. However, other ways to combine matching rules may also be used.

The match detector may comprise a demographic match evaluator for evaluating the first demographic data and the second demographic data in order to classify the pair of patient records as at least one of matching, not matching, or undetermined; and a clinical match evaluator for evaluating the first clinical property and the second clinical property if the pair of patient records is classified as undetermined. This way, the clinical property only needs to be extracted and/or evaluated in case the demographic information is not sufficient to determine whether the pair of patient records match or not. This reduces the amount of data processing. The clinical match evaluator may be configured to evaluate more clinical properties in order to obtain a match with a higher certainty.

The match detector may be arranged for detecting an incompatibility between the first clinical property and the second clinical property, using the set of matching rules. The knowledge of such an incompatibility, inconsistency, or contradiction may be used in several ways. First, the match detector may be arranged for automatically rejecting a match upon detecting the incompatibility. This allows improving the matching process. Second, the system may comprise a correction suggester for suggesting a user to correct the incompatibility. This way, the system may be used to improve the actual content of the patient records, by detecting incompatibilities in patient records which are classified as matching pairs of patient records.

The system may comprise a user input for enabling a user to indicate whether two undetermined patient records are to be matched. This way, when it is still not possible to determine whether a pair of patient records match or not, based on demographic and/or clinical data, the patient records may be subjected to manual processing.

The match detector may comprise an implementation of a combined algorithm for evaluating both the demographic data and the clinical properties. This is an efficient implementation of the match detector. Moreover, by combining the demographic information and the clinical information in a combined algorithm, the accuracy may be improved.

The clinical property extractor may comprise an image processing module for extracting the clinical property from at least one medical image. This way, clinical information comprised in medical image data may be used for the matching process.

The first and/or second clinical property may comprise at least one of: genotype data, blood group, antibody information, blood test, lab test, medical image-based information.

The system may be incorporated in a workstation, such as a medical workstation.

In another aspect, the invention provides a method of matching a pair of patient records comprising a first patient record and a second patient record, comprising:

extracting at least one first clinical property from clinical information contained in the first patient record and at least one second clinical property from clinical information contained in the second patient record;

detecting whether the first patient record and the second patient record relate to the same patient, based on the first clinical property, the second clinical property, and a set of matching rules representing persistency characteristics of clinical properties of patients.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the workstation, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

DETAILED DESCRIPTION OF EMBODIMENTS

In current approaches, if two records cannot be automatically linked or declared as different, they are placed on an exception list by the matching application and need to be reviewed by specialized registration personnel. The human intervention may entail manually comparing the two records to detect whether they belong to the same person or not. The registration personnel may also ask the patient if the records belong to him or her. It is often difficult and time-consuming to manually review and compare patient records describing many health episodes and spanning decades. This manual process is also error-prone, as people have relatively small attention windows and find it difficult to follow a large number of variables across many data sources. Also, it may be necessary to ask the patient for clarification, which is cumbersome.

The longer the exception list, the more time would be spent on manually reviewing records and eliminating false positives (records that seem to belong to the same patients but in fact belong to two different patients). A reduction of the exception list would save a lot of time, reduce costs and decrease the possibility of errors.

Figure 1:
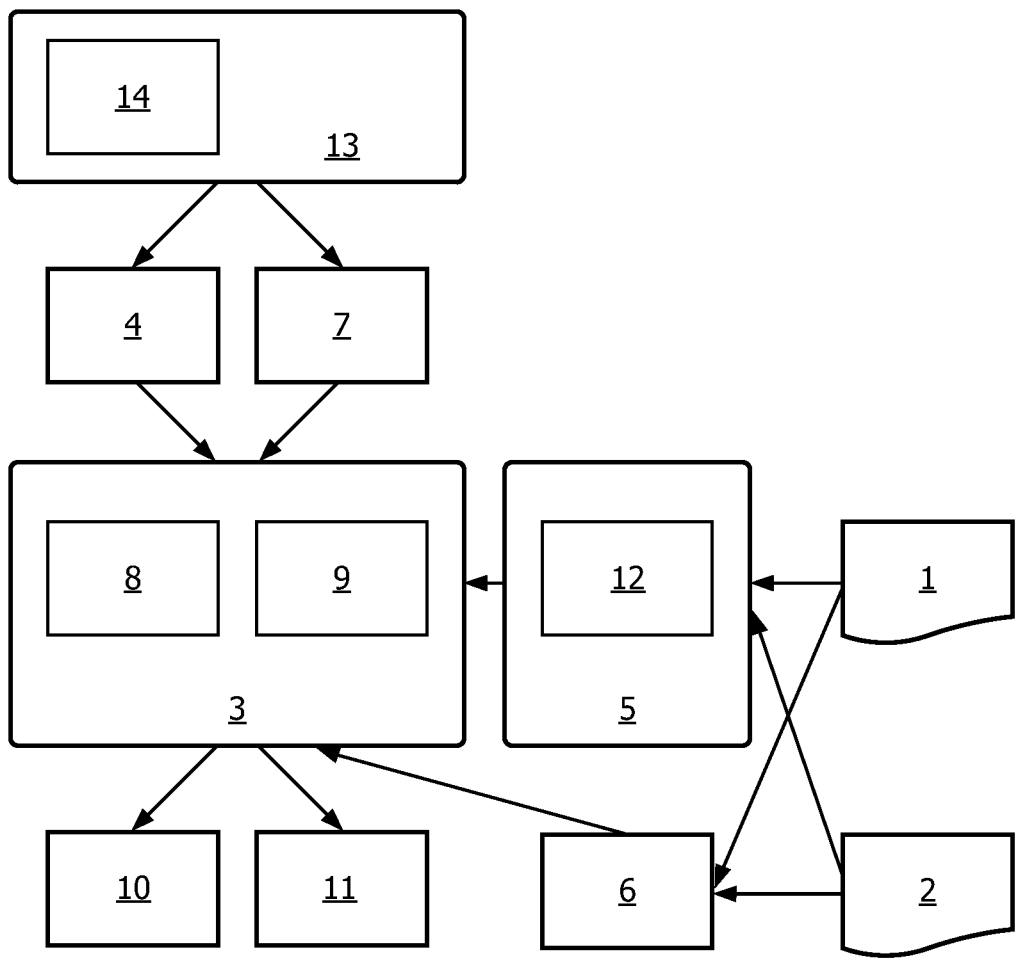
FIG. 1 is a block diagram of a system for matching a pair of patient records as belonging to the same individual or patient.

FIG. 1 illustrates aspects of a system for matching a pair of patient records as belonging to the same individual or patient. A pair of patient records comprises a first patient record 1 and a second patient record 2. A patient record may comprise several types of information relating to a single patient. For example, a patient record may contain demographic information identifying the patient, such as name, address, a local patient identifier, a social security number, insurance information, date of birth, sex. A patient record may further comprise clinical information, such as medical image data, lab results, blood group, test outcomes, diagnostic information. Patient records are typically created locally at a clinical organization. Consequently, different patient records may be created for the same patient at different clinical organizations. For improved treatment and diagnosis, it is necessary to combine the information about a patient in the different patient records. To this end, the patient records at the different clinical sites may be compared to find records belonging to the same patient. The system may comprise a set of matching rules 4 representing persistent characteristics of clinical properties of patients. An example of such a matching rule is that the blood group of a patient does not change. Another example is that after a vaccination, antibodies should be detectable in the blood. Other types of matching rules are described elsewhere in this description.

The system comprises a clinical property extractor 5 for extracting at least one first clinical property from clinical information contained in the first patient record 1 and at least one second clinical property from clinical information contained in the second patient record 2. These clinical properties may correspond to the clinical properties which are used in the matching rules 4. The system further comprises a match detector 3 for detecting whether the first patient record 1 and the second patient record 2 relate to the same patient. This is based on the first clinical property, the second clinical property, and the set of matching rules 4. More clinical properties and more matching rules may be used to detect whether a pair of patient records match. The first and second clinical property may relate to the same type of clinical property, for example blood group. Alternatively, the first and second clinical property may relate to different types of clinical property, for example blood group and genotype. The relationship between the different types of clinical property may be given by the matching rules 4.

The system may comprise a demographic property extractor 6 for extracting first demographic data from the first patient record 1 and second demographic data from the second patient record 2, wherein the match detector 3 is arranged for performing the detecting also based on the first demographic data and the second demographic data. To this end, the match detector 3 may be arranged for comparing the demographic data stored in both patient records 1,2. There are different ways in which the system may handle both demographic and clinical data. For example, the system may first compare the demographic data, and, if the demographic data is sufficiently similar or dissimilar, determine whether or not there is a match without evaluating the clinical data. To this end, the match detector 3 may comprise a demographic match evaluator 8 for evaluating the first demographic data and the second demographic data in order to classify the pair of patient records 1,2 as at least one of matching, not matching, or undetermined. The match detector may further comprise a clinical match evaluator 9 for evaluating the first clinical property and the second clinical property if the pair of patient records 1,2 is classified as undetermined by the demographic match evaluator 8.

The match detector 3 may be arranged for evaluating clinical data, even if the demographic data is identical, for preventing an accidental match between two persons with similar demographic data. The match detector may also be arranged for weighting the outcome of comparisons of clinical and demographic data. Alternatively, the set of matching rules 4 may comprise rules about both demographic and clinical properties; these rules and the properties used therein may be evaluated by an inference engine in the order indicated by said inference engine.

The match detector 3 may be arranged for detecting an incompatibility between the first clinical property and the second clinical property, using the set of matching rules 4. The match detector 3 may be arranged for automatically rejecting a match upon detecting the incompatibility.

The system may comprise a correction suggester 10 for suggesting a user to correct the incompatibility. The correction suggester 10 may be arranged to do the suggestion when a match is detected with a sufficient degree of uncertainty, while there are still one or more incompatibilities in the data. These incompatibilities might be the result of a mistake, which may be corrected.

The set of matching rules 4 may be associated with a set of corresponding weights 7. The match detector 3 may be arranged for determining a matching score for the pair of patient records 1,2, based on the set of matching rules 4 and the set of corresponding weights 7. The system may comprise a user input 11 for enabling a user to indicate whether the pair of patient records 1,2 relate to the same patient, if a result of the match detector 3 is undetermined. The match detector 3 may be implemented on the basis of a combined algorithm for evaluating both the demographic data and the clinical properties.

The clinical property extractor 5 may comprise an image processing module 12 for extracting the clinical property from at least one medical image. For example, image processing may be based on pattern recognition techniques. For example, a fracture in a bone may be detected. Also, the presence of an implant may be verified by using image processing techniques.

The system according to claim 1, wherein the first and/or second clinical property comprises at least one of: genotype data, blood group, antibody information, blood test, lab test, medical image-based information, diagnosis. The clinical property extractor 5 may thus be arranged for extracting such a property from the patient records 1 and 2.

The system may be implemented in a workstation, for example by means of software. The workstation may comprise user input means, such as keyboard and mouse, enabling a user to control the system, and a display for showing the results to a user. Storage means may be provided and a communications port, for example a network interface, for collecting contents of patient records from one or more external resources.

A tool 13 may be provided which enables a user to configure the system. To that end, the tool 13 comprises a user interface 14. The tool 13 may enable a user to indicate a set of clinical properties of patients, which are to be used in the matching process. Moreover, the tool 13 may enable the user to indicate the set of matching rules 4 representing persistent characteristics of the clinical properties. The rules are used to combine the clinical properties of the patients as extracted from the patient records. The tool 13 may provide a list of matching rules from which the user may select one or more matching rules. In addition or alternatively, the tool 13 may allow the user to enter one or more matching rules by means of an appropriate language which may be interpreted by the match detector 3.

Figure 2:
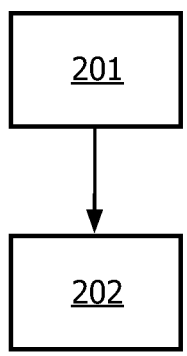
FIG. 2 is a flow chart illustrating a method of matching a pair of patient records as belonging to the same individual or patient.

FIG. 2 shows a flow chart illustrating aspects of a method of matching a pair of patient records comprising a first patient record and a second patient record. The method comprises a step 201 of extracting at least one first clinical property from clinical information contained in the first patient record and at least one second clinical property from clinical information contained in the second patient record.

The method further comprises a step 202 of detecting whether the first patient record and the second patient record relate to the same patient, based on the first clinical property, the second clinical property, and a set of matching rules representing persistency characteristics of clinical properties of patients. Modifications and/or extensions of the method may be implemented by the skilled person in view of the present description. The method may be implemented as a computer program product designed to run on a processor system.

The identity matching process may be extended by using clinical data with high identification value and temporal validity, in addition to the commonly used demographic data, for improving the automatic matching efficiency. One may statically decide on a set of clinical data attributes to search and extract from the pairs of records to be matched and on weights corresponding to each of those attributes. Examples of such attributes include blood group, genotype information, and/or presence of antibodies in blood. An example of genotype information is single-nucleotide polymorphism (SNP).

A more formal approach is to define a data model and a set of semantic relations and rules among the attributes that enable the detection of inconsistencies or obvious matches among the attributes to discern whether the two records belong to the same individual or not. In this case, more complex reasoning can be added to the comparison of simple attributes as mentioned above. For example, a patient that had a hip replacement or a serious fracture cannot have a normal X-Ray of the same area at a later time. A set of modules managing the sets of rules and the relevant clinical data need to be built as well.

Based on this additional data the success rate of the automatic matching can be increased.

Alternatively, the record matching process may be extended with an algorithm that scans the exception list, which contains records that could not be automatically accepted or rejected as matches, based on an existing identity matching system, and that uses the semantics and content of the clinical data in the patient records to be matched to discern whether the record pairs could belong to the same patient. When inconsistencies are detected in a pair of records, they are automatically declared as mismatches and removed from the exception list for manual review. An alternative is to multiply a contribution to the matching score by a specific weight, thereby reducing the score accordingly for each inconsistency. When the score of the record pair falls below the reject threshold, the potential match is rejected.

Demographic data may be used in the matching process. However, demographic data changes and may contain errors. In the registration process, numeric data can be erroneously introduced, names can be misspelled, patients can make mistakes when providing their addresses, can provide different nicknames, etc. Additionally, the demographic data can change: the address of a patient may change, or the last name of a patient may change after marriage. As a result, mismatches in demographic data are quite frequent. These errors or changes can decrease the performance of the matching algorithm and increase the number of records placed on the exception list.

On the other hand, several clinical data items allow identifying a person, or allow the detection of a mismatch. Genomic data (genotype), various lab data such as blood group, detected antibodies and persistent viral infections, known allergies, image data and other measurements may be used in the matching process.

Biometric identification data, if collected, may also be used for identification.

In an example of a matching process, a record from a hospital A may be compared to a selection of records from another hospital B that are potential matches (for example, because some relevant demographic data matches). After the selection of potential matches, the matching algorithm may be applied between the record from hospital A and each of the selected records from hospital B.

A number of steps may be taken to utilize the clinical data for identity matching.

A profile describing the clinical data items that should be extracted may be created as well as a set of rules describing the way these items may be compared to other items in the corresponding records. This set of rules may be used in the matching process. Such rules may include, for example, "match existence of antibodies to prior known vaccination", "match visible signs on an XRAY to previous broken leg". A data model and a set of semantic relations among the various data items can also be used.

Weights may be assigned to each of the clinical data items and/or rules to be used in the matching algorithm.

To match a record from a hospital A to a group of potentially matching records from a hospital B:

1. The patient record from hospital A is processed to extract data that can be used for identification of the patient, according to the profile.

2. The extracted data may be stored in the PR (patient registry) or in a dedicated storage (the patient identification registry, PIR), together with the local identifier of the record. The data can be used again whenever this record is selected to be compared to a record from a different hospital, in which case the patient identification registry content needs to be persistent, or it can be retrieved on the fly, in which case only a limited storage is necessary.

3. The potentially matching patient records from hospital B are processed to extract the data that can be used for identification of the patient, according to the profile. This data may be extracted from the records at hospital B, as in steps 1 and 2, or from the PR or PIR of hospital B when the data was stored there before.

4. Next, the matching may be carried out according to the algorithm. The demographic data may be matched according to known procedures. The clinical data may be matched according to the rules set in the defined profile. A total score may be computed and a decision taken to match the two records or reject the match.

The same steps may be repeated for all pairs of records to be matched.

An example algorithm for scanning the exception list compares clinical data items with high identity value between the records to be matched, and automatically detects inconsistencies, and upon detecting an inconsistency, lowers the matching score (which then can fall below the reject threshold) or removes the pair of records from the exception list (rejects the potential match).

Two types of relevant identifiers may be distinguished: First, persistent information whose values do not change over time, such as blood group, persistent genetic information (such as genotype). Second, known clinical events and attributes that, after onset, are persistent, such as surgery, chronic diseases, various virus infections. These can be used to detect inconsistencies in record data that is more recent.

Figure 3:
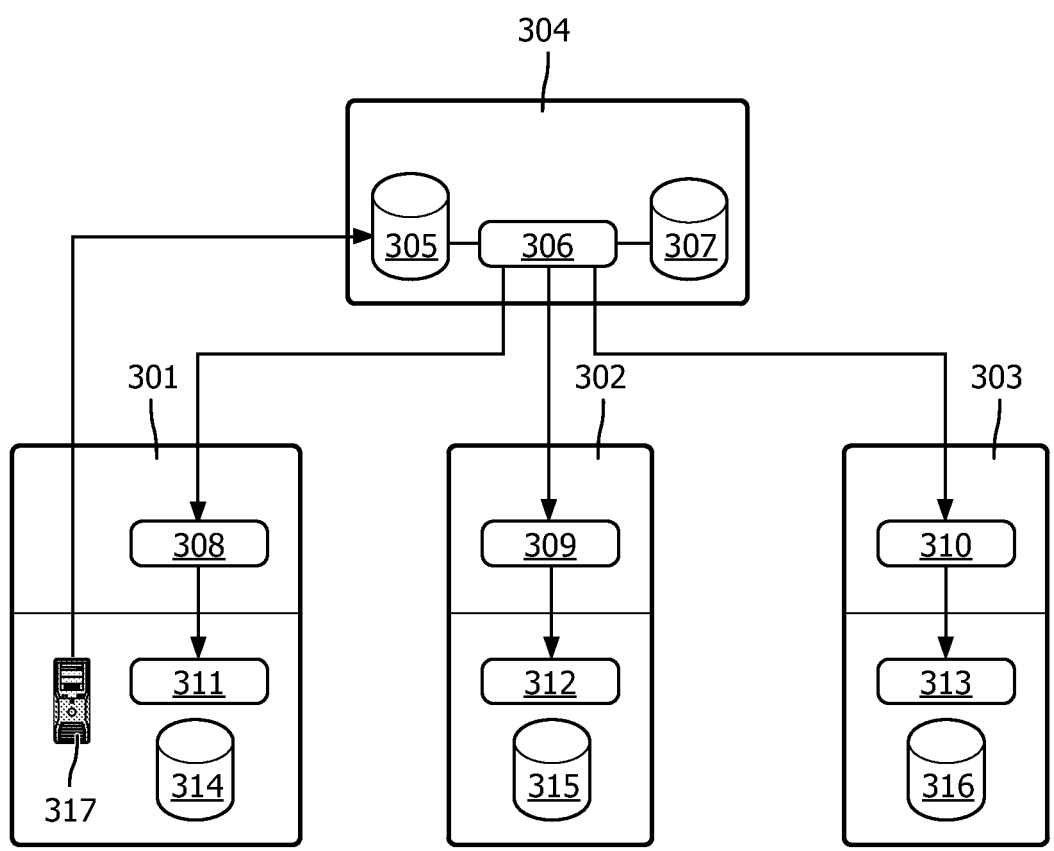
FIG. 3 is a diagram of a distributed healthcare information system.

FIG. 3 illustrates an example of how the system may be deployed in a system covering a plurality of hospitals or organizations 301, 302, and 303. The organizations each have a storage server 314, 315, 316 storing patient records 311,312,313. A client 317 in one of the hospitals 301 may be configured to request all patient records relating to a patient X of patient record 311. This request is made to a patient registry 305 (or PIX manager). The patient registry 305 may store patient identifiers at other organizations 302,303 for the same patient. If the information for the requested patient X is not yet available in the patient registry 305, the query may be forwarded to the different servers 309,310 of organizations 302,303 by server 306. Server 306 has access to the profile 307. Server 306 contacts server 308 of organization 301 to extract the data from the patient record 311 that can be used for the identification according to the profiles 307. Subsequently, server 306 requests potentially matching patient records 312,313 from servers 309 and 310, and performs the matching according to the profile 307. Matched patients can be stored in the patient registry 305 and returned to the requesting client 317.

It will be appreciated that the invention also applies to computer programs, particularly computer programs on or in a carrier, adapted to put the invention into practice. The program may be in the form of a source code, an object code, a code intermediate a source code and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method of determining whether a first patient record and a second patient record stored in a computer-readable form relate to the same patient, comprising:

extracting a first plurality of clinical properties from clinical information in the first patient record;

extracting a second plurality of clinical properties from clinical information in the second patient record;

distinguishing persistent clinical properties of the first plurality of clinical properties from non-persistent clinical properties of the first plurality of clinical properties;

for each persistent property of the first plurality of clinical properties:

determine if the persistent property is incompatible with at least one clinical property of the second plurality of clinical properties, wherein an attribute type of the at least one clinical property of the second plurality of clinical properties is different from an attribute type of the persistent property;

if the persistent property is incompatible with the clinical property of the second plurality of clinical properties, determine that the first and second patient records do not correspond to the same patient;

else, determine and store a matching score for the persistent property and the second plurality of clinical properties, and repeat for the next persistent property;

for each non-persistent property of the first plurality of clinical properties:

determine and store a matching score for the non-persistent property and the second plurality of clinical properties, and repeat for the next non-persistent property;

extracting a first plurality of demographic properties from demographic information in the first patient record;

extracting a second plurality of demographic properties from demographic information in the second patient record;

for each demographic property of the first plurality of demographic properties:

determine and store a matching score for the demographic property and the second plurality of demographic properties, and repeat for the next demographic property;

determining whether the first patient record and the second patient record relate to the same patient based on the matching scores of the first plurality of persistent properties, the first plurality of non-persistent properties, and the first plurality of demographic properties; and if the first patient record and the second patient record relate to the same patient, recording this relationship in a non-transitory computer-readable medium so that a subsequent access to records of this same patient includes access to the first patient record and the second patient record.

2. The method of claim 1, including selecting the second patient record based on at least one demographic property of the first property and at least one matching demographic property of the second patient.

3. The method of claim 1, wherein determining whether the first patient record and the second patient record relate to the same patient is based on a composite score that is based on a weighting of the matching scores.

4. The method of claim 3, wherein the weighting of the matching scores includes one of the weightings based on a temporal relationship between the first and second patient records.

5. The method of claim 3, wherein determining whether the first patient record and the second patient record relate to the same patient is based on whether the composite score exceeds a threshold score.

6. The method of claim 5, wherein, if the composite score is below the threshold score, but above a reject threshold, the method includes providing a suggestion to a user to facilitate determining whether the first patient record and the second patient record relate to the same patient.

7. The method of claim 5, wherein, if the composite score is below the threshold score, but above a reject threshold, the method includes receiving a user input to facilitate determining whether the first patient record and the second patient record relate to the same patient.

8. The method of claim 1, wherein extracting the clinical properties includes processing a medical image to determine at least one of the clinical properties.

9. The method of claim 1, wherein determining at least one matching score for a clinical property of the first plurality of clinical properties is based on an assessment of more than one clinical properties of the second plurality of clinical properties.

10. A non-transitory computer-readable medium that includes a program that, when executed by a processor, causes the processor to:
extract a first plurality of clinical properties from clinical information in the first patient record;
extract a second plurality of clinical properties from clinical information in the second patient record;
distinguish persistent clinical properties of the first plurality of clinical properties from non-persistent clinical properties of the first plurality of clinical properties;
for each persistent property of the first plurality of clinical properties:
determine if the persistent property is incompatible with at least one clinical property of the second plurality of clinical properties, wherein a type of the at least one clinical property of the second plurality of clinical properties is different from a type of the persistent property;
if the persistent property is incompatible with the clinical property of the second plurality of clinical properties, determine that the first and second patient records do not correspond to the same patient;
else, determine and store a matching score for the persistent property and the second plurality of clinical properties, and repeat for the next persistent property;
for each non-persistent property of the first plurality of clinical properties:
determine and store a matching score for the non-persistent property and the second plurality of clinical properties, and repeat for the next non-persistent property;
extract a first plurality of demographic properties from demographic information in the first patient record;
extract a second plurality of demographic properties from demographic information in the second patient record;
for each demographic property of the first plurality of demographic properties:
determine and store a matching score for the demographic property and the second plurality of demographic properties, and repeat for the next demographic property;
determine whether the first patient record and the second patient record relate to the same patient based on the matching scores of the first plurality of persistent properties, the first plurality of non-persistent properties, and the first plurality of demographic properties; and
if the first patient record and the second patient record relate to the same patient, record this relationship in a computer-readable form so that a subsequent access to records of this same patient includes access to the first patient record and the second patient record.

11. The medium of claim 10, wherein the program causes the processor to select the second patient record based on at least one demographic property of the first property and at least one matching demographic property of the second patient.

12. The medium of claim 10, wherein the program causes the processor to determine whether the first patient record and the second patient record relate to the same patient by determining a composite score that is based on a weighting of the matching scores.

13. The medium of claim 12, wherein the program causes the processor to weight at least one of the matching scores based on a temporal relationship between the first and second patient records.

14. The medium of claim 12, wherein the program causes the processor to determine whether the first patient record and the second patient record relate to the same patient based on whether the composite score exceeds a threshold score.

15. The method of claim 14, wherein, if the composite score is below the threshold score, but above a reject threshold, the program causes the processor to provide a suggestion to a user to facilitate determining whether the first patient record and the second patient record relate to the same patient.

16. The method of claim 14, wherein, if the composite score is below the threshold score, but above a reject threshold, the program causes the processor to receive a user input to facilitate determining whether the first patient record and the second patient record relate to the same patient.

17. The medium of claim 10, wherein the program causes the processor to extract at least one of the clinical properties by processing a medical image.

18. The medium of claim 10, wherein the program causes the processor to determine at least one matching score for a clinical property of the first plurality of clinical properties based on an assessment of more than one clinical properties of the second plurality of clinical properties.

19. A system for matching a pair of patient records as belonging to the same individual or patient, wherein the pair of patient records comprises a first patient record and a second patient record, the system comprising:
- a set of matching rules representing persistent and non-persistent properties of a plurality of clinical properties of patients;
- a clinical property extractor that extracts a first plurality of clinical properties from clinical information contained in the first patient record, and a second plurality of clinical properties from clinical information contained in the second patient record;
- a match detector that:
  - distinguishes persistent clinical properties of the first plurality of clinical properties from non-persistent clinical properties of the first plurality of clinical properties;
  - for each persistent property of the first plurality of clinical properties:
    - determines if the persistent property is incompatible with at least one clinical property of the second plurality of clinical properties, based on the matching rules of this persistent property, wherein an attribute type of the at least one clinical property of the second plurality of clinical properties is different from an attribute type of the persistent property;
    - if the persistent property is incompatible with the clinical property of the second plurality of clinical properties, determines a non-match;
    - else, determines and stores a matching score for the persistent property and the second plurality of clinical properties based on the matching rules of this persistent property and repeat for the next persistent property;
  - for each non-persistent property of the first plurality of clinical properties:
    - determines and stores a matching score for the non-persistent property and the second plurality of clinical properties based on the matching rules of this non-persistent property, and repeat for the next non-persistent property;
- a demographic property extractor that extracts first demographic data from the first patient record and second demographic data from the second patient record,
- a demographic match evaluator that:
  - for each demographic property of the first plurality of demographic properties:
    - determines and stores a matching score for the demographic property and the second plurality of demographic properties, and repeat for the next demographic property; and
- a clinical match evaluator that:
  - determines whether the first patient record and the second patient record relate to the same patient based on the matching scores of the first plurality of persistent properties, the first plurality of non-persistent properties, and the first plurality of demographic properties; and
  - if the first patient record and the second patient record relate to the same patient, records this relationship in a non-transitory computer-readable medium so that a subsequent access to records of this same patient includes access to the first patient record and the second patient record.

20. The system of claim 19, wherein the system selects the second patient record based on at least one demographic property of the first plurality of demographic properties and at least one matching demographic property of the second plurality of demographic properties.

* * * * *